United States Patent [19]
Vari et al.

[11] Patent Number: 5,377,676
[45] Date of Patent: Jan. 3, 1995

[54] METHOD FOR DETERMINING THE BIODISTRIBUTION OF SUBSTANCES USING FLUORESCENCE SPECTROSCOPY

[75] Inventors: Sandor G. Vari, Encino; Warren S. Grundfest, Los Angeles, both of Calif.

[73] Assignee: Cedars-Sinai Medical Center, Los Angeles, Calif.

[21] Appl. No.: 39,991

[22] Filed: Mar. 30, 1993

Related U.S. Application Data

[63] Continuation-in-part of Ser. No. 679,766, Apr. 3, 1991, Pat. No. 5,318,023, and Ser. No. 891,586, Jun. 1, 1992.

[51] Int. Cl.$^6$ .............................................. A61B 5/00
[52] U.S. Cl. ...................................... 128/634; 128/633; 128/665; 606/2; 606/14
[58] Field of Search ............................. 606/2, 13–15; 128/633–634, 664–665

[56] References Cited

U.S. PATENT DOCUMENTS

| | | | |
|---|---|---|---|
| 4,556,057 | 12/1985 | Hiruma et al. | 128/634 |
| 5,074,306 | 12/1991 | Green et al. | 128/664 |
| 5,111,821 | 5/1992 | Potter | 128/664 |
| 5,131,398 | 7/1992 | Alfano et al. | 128/665 |

OTHER PUBLICATIONS

Castro, D. J. et al., "Biodistribution Of Rhodamine–123 In Nude Mice Heterotransplanted With Human Squamous Cell Carcinomas," *Laryngoscope*, 102:868–74 (Aug. 1992).

Unsold, E. et al., "Fluorescence Diagnosis And Photodynamic Therapy-Evaluation Of Sensitizers By Comparison Of Their Pharmacokinetics," *Photosensitization Molecular, Cellular and Medical Aspects* (NATO ASI Series), Series H: Cell Biology, vol. 15, pp. 473–478 (1988).

Tata, D. B. et al., "Fluorescence Polarization Spectroscopy And Time-Resolved Fluorescence Kinetics Of Native Cancerous And Normal Rat Kidney Tissues," *Biophys. J.*, 50:463–69 (Sep. 1986).

Richter, A. M. et al., "Biodistribution Of Tritiated Benzoporphyrin Derivative ($^3$H–BPD–MA), A New Potent Photosensitizer In Normal And Tumor Bearing Mice," *Photochem. and Photobiol.*, 5:231–244 (1990).

Larson, S. M., "Clinical Radioimmunodetection, 1978–1988: Overview And Suggestions For Standardization Of Clinical Trials," *Cancer Research*, (Suppl.), 50:892S–898S (Feb. 1990).

del Rosario, R. D. and Wahl, R. L., "Disulfide Bond—Targeted Radiolabeling: Tumor Specificity Of A Streptavidin-Biotinylated Monoclonal Antibody Complex," *Cancer Research (Suppl.)*, 50:804S–808S (Feb. 1990).

Vernon, D. I. and Bronw, S. B., "The Preparation Of Radiolabeled Porphyrins And Their Use In Studies Of Photodynamic Therapy," *Photochem. and Photobiol.*, 4(5):581–586 (1987).

Andreoni, A., "Time–Resolved Luminescence Spectroscopy Of Photosensitizers Of Biomedical Interest", *Photochem. and Photobiol*, 52(2):423–430 (1990).

Jori, G., "Photosensitized Processes In Vivo: Proposed Phototherapeutic Applications", *Photochem. and Photobiol*, 52(2):439–443 (1990).

Baumgartner, R. et al., "Pharmacokinetics Of Fluorescent Polyporphyrin Photofrin II In Normal Rat Tissue (List continued on next page.)

Primary Examiner—Randall L. Green
Assistant Examiner—P. Zuttarelli
Attorney, Agent, or Firm—Lyon & Lyon

[57] ABSTRACT

A method is disclosed for determining the biodistribution of substances using fluorescence spectroscopy. A photosensitizing agent or other intrinsically fluorescent agent, or an agent labeled with an extrinsic fluorophor is administered to a subject. A fiberoptic probe integrated with an excitation light source illuminates the examined tissue and causes fluorescence. The fluorescence is recorded by a spectrograph and plotted as a spectral curve. The intensity ratio (S1/S2) for the fluorescence from the photosensitizing agent (S1) and autofluorescence (S2) for the examined tissue is used as an index for drug presence and compared with the intensity ratio at the same wavelengths for various tissues.

10 Claims, 10 Drawing Sheets

OTHER PUBLICATIONS

And Rat Bladder Tumor," *Photochem. and Photobiol.*, 55(4):569–574 (1992).

Russell, D. A. et al., "A Comparison Of Fluorescence Excitation Sources For In Vivo Pharmacokinetic Measurements Of The Photodynamic Therapy Model Photosensitizer Hematoporphyrin IX," *Canadian Journal of Applied Spectroscopy*, 36(5):103–107 (1991).

Gomer, C. J. and Dougherty, T. J., "Determination Of [$^3$H]– and [$^{14}$C] Hematoporphyrin Derivative Distribution In Malignant And Normal Tissue," *Cancer Research*, 39:146–157 (1979).

METHOD FOR DETERMINING THE BIODISTRIBUTION OF SUBSTANCES USING FLUORESCENCE SPECTROSCOPY

This application is a continuation-in-part application of copending applications Ser. Nos. 07/679,766 filed Apr. 3, 1991 now U.S. Pat. No. 5,318,023 and 07/891,586 filed Jun. 1, 1992 pending.

FIELD OF THE INVENTION

The present invention relates generally to a method for determining the biodistribution of substances using fluorescence spectroscopy.

BACKGROUND

"Photodynamic Therapy" (PDT) is based upon the selective retention of porphyrin agents by neoplastic tissues. When injected intravenously, porphyrins localize at higher levels in malignant tumor tissues than in normal tissues. These same porphyrins also emit a characteristic dual-peaked red fluorescence after being exposed to light containing the appropriate wavelength to excite fluorescence. Porphyrins can be activated by light to catalyze the production of singlet oxygen from available triplet oxygen. Although the exact mechanism of necrosis is unclear, it has been suggested that the reactive singlet oxygen oxidizes unsaturated carbon-carbon bonds in amino acids and fatty acids. The ensuing loss of the structural integrity of cellular macromolecules results in cytocidal effects and tumor necrosis.

The initial experience with PDT centered on hematoporphyrin derivative (HPD) because of its attractive properties of tumor localization, low toxicity, photodynamic activity and absorption in the red spectrum (~630 nm). Notwithstanding these advantages, however, HPD has one main disadvantage, that being its tendency to accumulate in the skin and cause a prolonged skin photosensitivity. In recent years, however, a more purified version of HPD, known commercially as Photofrin, Porfimer Sodium (hereinafter "Photofrin") has been used in clinical trials. Photofrin contains dihematoporphyrin ether (DHE), the agent primarily responsible for the tumor localizing and photosensitizing activity of the drug. After irradiation by blue light, Photofrin emits an intense dual peaked red fluorescence that can be detected and analyzed.

Benzoporphyrin derivative monoacid-A (BDP-MA), another photosensitizing agent, is a benzo-derivative of photoporphyrin IX. In addition to its powerful phototoxicity, BPD-MA has a characteristic absorption maximum around 700 nm, which permits use of light with greater penetration depths. BPD-MA also appears to have lower skin concentrations and a shorter accumulation time at therapeutic levels than HPD, resulting in dramatically decreased photosensitivity of the skin of animals undergoing photodynamic therapy. After excitation by blue light, BPD-MA emits a characteristic red fluorescence peak at approximately 690 nm.

Many other compounds, such as modified porphyrins, chlorins, phthalocynines and purpurins may be useful as photosensitizers. In addition, silicon naphthalocynines, texaphyrins and other extended macrocycles containing tetrapurroles such as porphycenes and plotyrins may also be used as photosensitizers.

PDT optimization, however, requires a knowledge of the time course of drug concentration and selectivity of drug for tumors. In spite of significant recent progress, many of the detailed chemical and biochemical aspects of porphyrin sensitized PDT remain to be elucidated. These include the mechanism of its absorption, distribution and clearance from the body as well as the precise nature of the localizing and photosensitizing components.

Much of the research involving the determination of porphyrin tissue levels has involved radiolabelled porphyrin preparations ($^{14}C$ or $^{3}H$) and/or the chemical extraction of the porphyrin agent from tissue biopsies. These techniques have a number of limitations, including exposing the patient to the hazards of radioactivity, the need to sacrifice a large number of animals and the poor spatial and temporal resolution practically obtainable. Additional problems and limitations are encountered in radiolabelling the photosensitizer. For instance, tritrium labelled HPD prepared by catalytic exchange may exchange again in vivo thereby obscuring results. On the other hand, tritium catalytic exchange of whole HPD, as opposed to one of its simple precursors (i.e., HP), could result in the labelling of any one or more of the numerous components in HPD. Although $^{14}C$ photosensitizers theoretically should not undergo an in vivo exchange, unequal data has been obtained in pharmacological studies. Laser induced fluorescence measurements of drug biodistribution overcomes many of these disadvantages.

SUMMARY OF THE INVENTION

The present invention involves a laser light source (pulsed and continuous wavelength) and/or a non-laser excitation light source (adjustable wavelength) of any wavelength, and/or non-coherent light based fiber-optic excitation/detection system to induce fluorescence of any drug or any extrinsic fluorophor labeled drug, and ratio fluorometry with:

1. Spectrograph and optical multichannel analyzer;
2. Silicon photo cells to measure the intensity of the light source and of the back scattered excitation signal. Photomultiphers optimized for a particular detection wavelength and equipped with a band-pass filter to measure the collected fluorescence in different wavelength intervals;
3. Bandpass filters and photodiodes; and
4. Software for real time, in situ measurements.

According to one embodiment of the invention, a photosensitizing agent is administered to a subject. The photosensitizing agent may be a porphyrin or derivative thereof such as Photofrin or BPD-MA, or any other substance exhibiting fluorescence or labeled with an extrinsic fluorophor. The region to be examined is then illuminated with a beam of monochromatic light and/or incoherent light filtered to a specific wavelength from a fiber optic probe, and the emitted fluorescence is recorded by a spectrograph and plotted as a spectral curve. The intensity ratio (S1/S2) of the photosensitizer induced fluorescence (S1) and autofluorescence (S2) for the examined tissue is compared with the intensity ratio at the same wavelengths for primary tumor and normal tissue to determine the relative biodistribution of the agent.

The apparatus for the present invention, according to another embodiment, includes a light source, a spectrograph, a video camera, a digitizer, a computer, and a display means for measuring and comparing the intensity of the emitted light over a plurality of wavelengths.

The apparatus of the present invention according to yet another embodiment, includes a light source, optical filters, a photo detector and a display means for measuring the emitted light at different wavelengths. The method may include visual guidance through a flexible or rigid endoscope, and a video interface to instantly display the results on a video monitor during the scanning. As such, the local measurement may be stored together with a visual picture of the tissue, and later retrieved for further study. Because of their superior strength and fatigue resistance, aluminum, gold or metal-coated fibers are especially attractive in this method. Metal-coated fibers can also be used in an x-ray imaging environment. It is to be understood however, that other embodiments may be utilized and that structural changes may be made without departing from the scope of the invention. The following detailed description is therefore, not to be taken in a limiting sense, and the scope of the present invention is best defined by the appended claims.

It is a general object of the present invention to provide a method for determining the biodistribution of substances.

It is also a general object of the present invention to provide a method for determining the absorption, distribution and excretion of drugs in a body.

It is another object of the present invention to provide a method for determining the biodistribution of substances using fluorescence spectroscopy.

It is a further object of the present invention to provide a method for determining the absorption, distribution and excretion of drugs in a body using fluorescence spectroscopy.

It is still another object of the present invention to provide a method for determining the biodistribution of photosensitizing agents using fluorescence spectroscopy.

DETAILED DESCRIPTION OF THE INVENTION

The present invention is directed to a method for determining the biodistribution of drugs using fluorescence spectroscopy.

The experimental arrangement used to measure the fluorescence spectra during abdominal exploration included a Helium-cadmium laser (Omnichrome, Chino, Calif.) operating at 442 nm as an excitation source. A 400 micron core diameter fiber was directed at the tissue in contact mode producing a low power (17 mW) illumination. Using the same fiber, reflected and emitted light was returned to the input of a SPEX 500 spectrometer (1422 G EG&G).

Laser output was reflected at a right angle by a dichroic mirror (HR/442 nm—H7>500 nm, CVI, New Mexico) and was focused at the input of a 400 micron core diameter fiberoptic probe. The excitation output of the laser at the distal end of the fiber was 17 mW. Fluorescence was collected using the same fiber and was transmitted through the dichroic beamsplitter and guided via a fiber bundle to a 0.5 spectrograph (100 g/mm diffraction grating with a split width of 50 microns). The light was then imaged at the modified output port. A 1024 element linear diode array detector (EG&G 1422G) was attached to the exit port, and the signal was directed to a multichannel intensifier. A longpass glass filter (Schott GG475) was used to exclude the excitation light from the detector and conversions were made by an analog to digital converter and automatically stored by a computer. Final data were displayed on the screen of the optical multichannel analyzer (OMA III, EG&G) and saved on a 20 Mb Winchester hard disc. Background spectra were recorded before excitation and subtracted from the resulting data. The detection system, including the detector attenuation filter, lenses and spectrograph, was not altered or corrected for a uniform spectral response.

Figure 1:
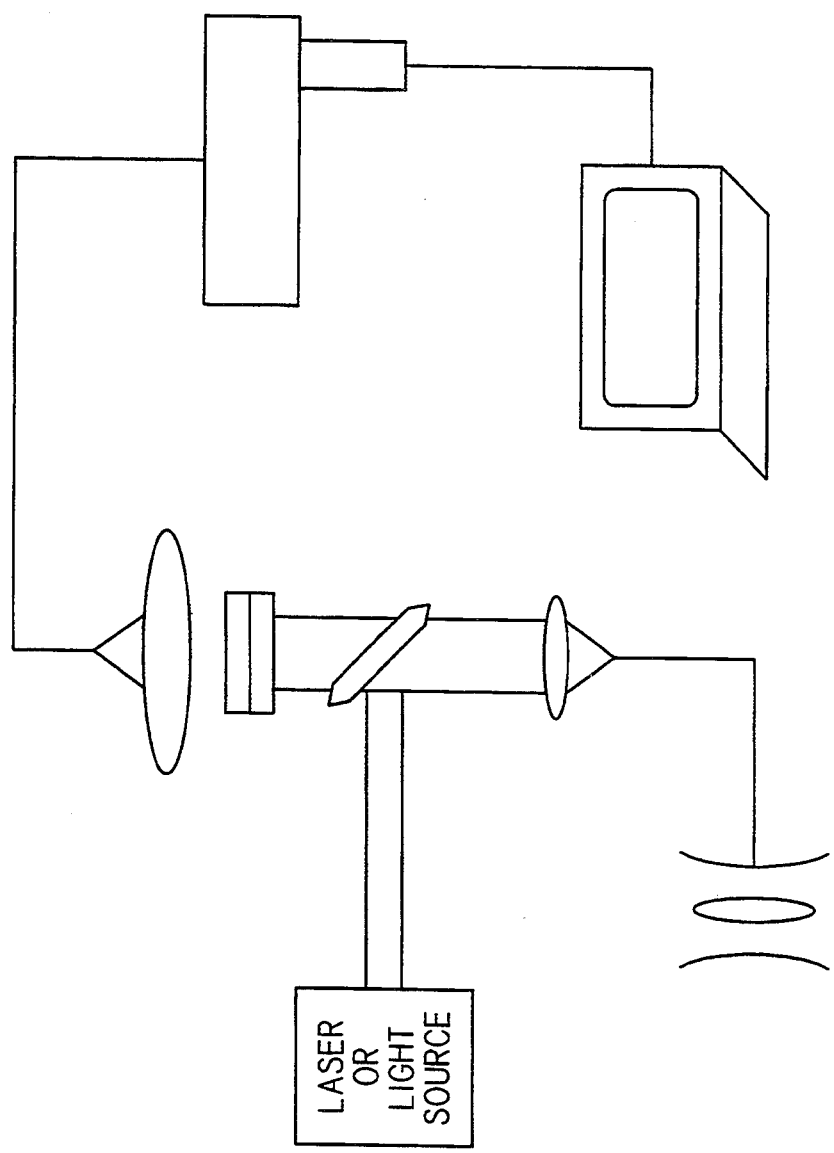
FIG. 1 is a schematic diagram of an excitation/detection system for biodistribution measurements.
Figure 2:
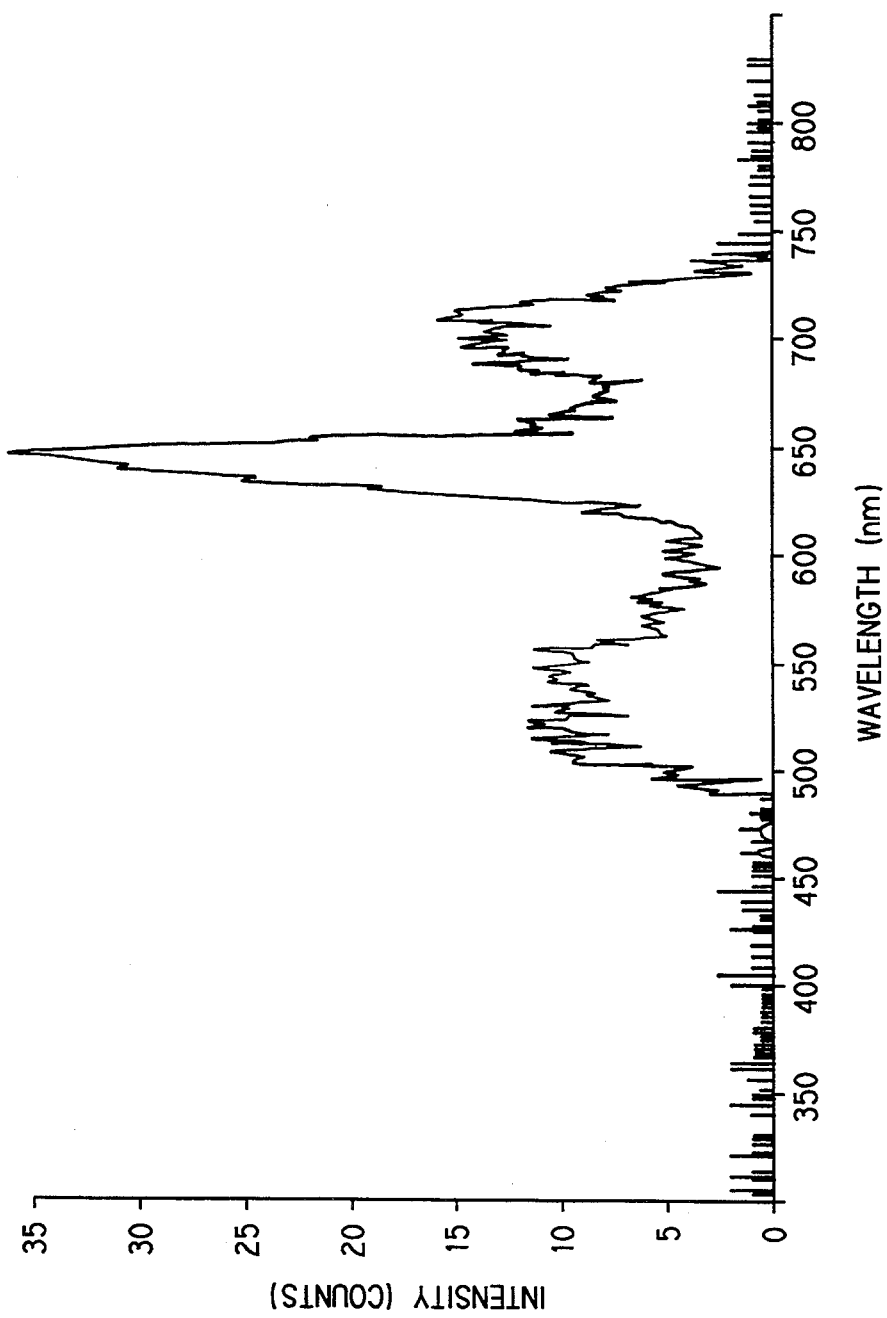
FIG. 2 is the fluorescence spectrum of Photofrin.
Figure 3:
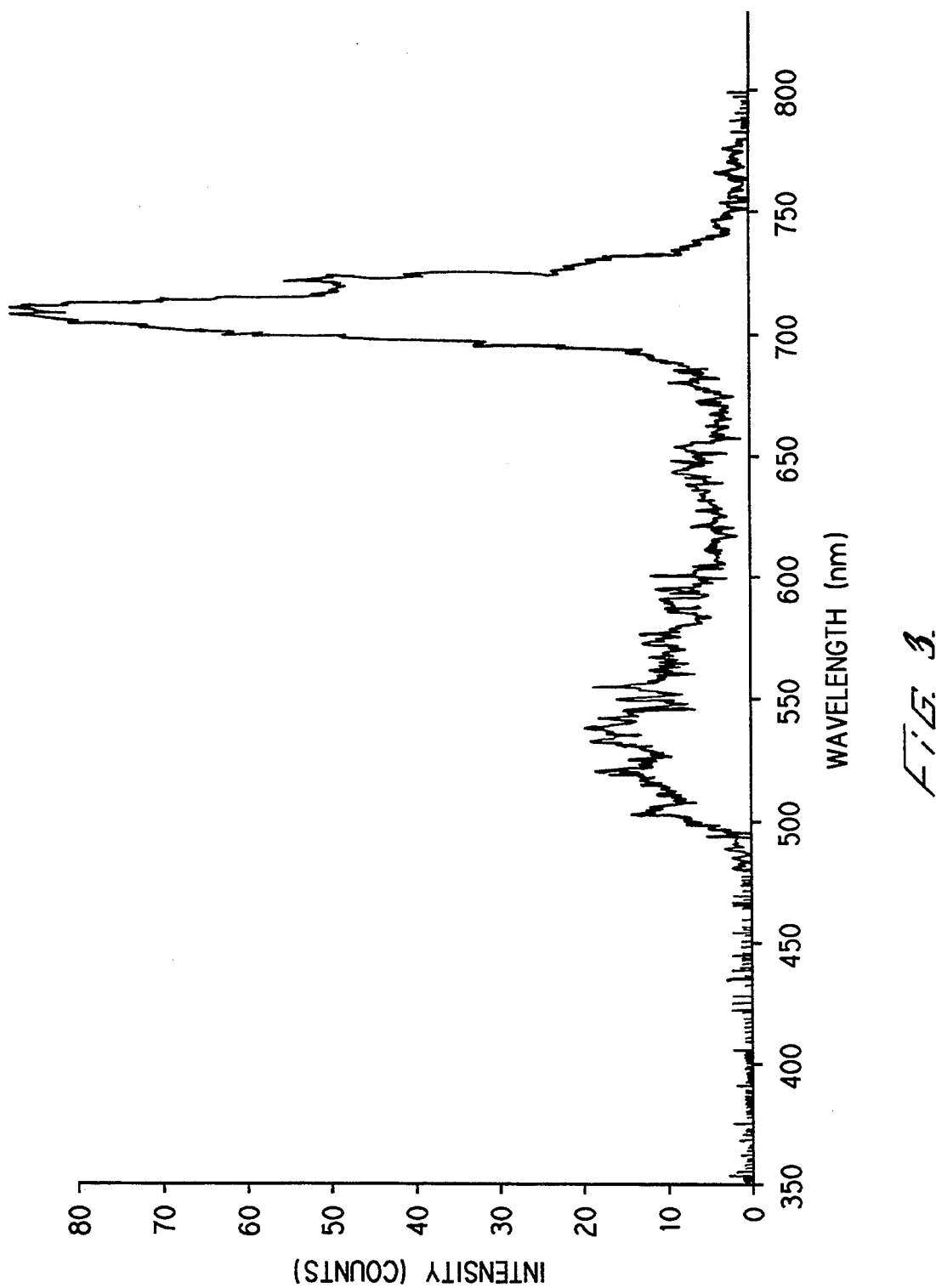
FIG. 3 is the fluorescence spectrum of BPD-MA.

Spectra from the surfaces of tumor (T), skin (S), muscle (M), liver (L), kidney (K), spleen (Sp), stomach (St), small bowel (SB) and large bowel (LB) were acquired and analyzed by the OMA. Signals from the OMA were then displayed on a screen for immediate examination. (FIG. 1 is a schematic representation of this experimental arrangement.) A series of spectra for Photofrin and BPD-MA were recorded from photosensitized animals. (FIGS. 2 and 3). The fluorescence intensities at 540 nm (auto-fluorescence) and 630 nm (Photofrin) or 690 nm (BPD-MA) were simultaneously monitored at three sites for each organ. By using the ratio of these intensities, ($I_{630\ nm}/I_{540\ nm}$) or ($I_{690\ nm}/I_{540\ nm}$), a relative value could be assigned to each area studied. In addition, this intensity ratio eliminated any geometric factor (fiber position) influence in the calibration, as well as calibration errors. The corresponding intensity ratios were used as an index for drug presence in the various tissues.

The fluorescence emitted from cancerous and normal tissues of male Lobund-Wistar rats was investigated (Lobund Laboratory, Notre Dame University, Id.). All tumors were subcutaneously implanted by inoculating $10^5$ viable cells of Pollard rat prostatic adenocarcinoma (PA-III) into the right flank of each animal. This tumor model was selected because it is known to metastasize uniformly and spontaneously from extravascular sites only through ipsilateral lymphatic channels. Because of this tumor's unique, predictable spread, the contralateral side of the animal could be used as a control. In addition, cancer detection is facilitated with this model because rats with PA-III cells survive beyond forty days after implantation without evidence of physical impairment.

A. Photofrin and Laser Induced Fluorescence Spectroscopy (LIFS)

After forty-two days of observation, Photofrin (QLT Phototherapeutics, Inc., Vancouver, Canada) was administered intraperitoneally to forty-one animals 24-48 hours prior to surgical exploration in doses ranging from 0.25-7.5 mg/kg. Six animals were injected 24 hours prior to surgical exploration with 0.75 mg/kg of Photofrin. Thirty animals were injected with six different concentrations of Photofrin 48 hours prior to surgical exploration (7.5 mg/kg (n=5), 2.5 mg/kg (n=4), 1.5 mg/kg (n=3), 0.75 mg/kg (n=11), 0.50 mg/kg (n=4), and 0.25 mg/kg (n=3)). Five animals which had not been inoculated with PA-III were injected with 0.75 mg/kg 48 hours prior to surgical exploration, and served as a control.

The animals were anesthetized with ketamine 40 mg/kg and Xylazine 5.0 mg/kg intraperitoneally, and the abdomens opened through a midline incision. LIFS exploration of the abdominal and inguinal area were performed. Ipsilateral and contralateral detection was directed to the site of lymph nodes adjacent to the inguinal ligament. From this point, areas were scanned in contact mode along the aorta to the para-aortic and renal lymph nodes (one spectra/16 milliseconds, 3-4 detection sites, going back and forth. Otherwise, the number of sites could increase.) The contralateral site was scanned in the same manner. Metastatic detection was performed during abdominal exploration of the renal, para-aortic, and iliac lymph nodes after laparotomy.

Corrected background fluorescence spectra were obtained in free running mode from the surface of the primary tumor, lymph nodes with metastatic neoplasm, as well as from the following organs: liver (L), spleen (Sp), kidney (K), stomach (St), small bowel (SB) and foot-pad skin (S). Suspected malignant tissues were removed for histological examination. The samples were fixed in formalin (10%) and embedded in paraffin.

RESULTS

TABLE I

BIODISTRIBUTION ANALYSIS OF PHOTOFRIN 48 HOURS AFTER INJECTION

| TISSUE | DOSE 7.5 mg/kg n = 5 | DOSE 2.5 mg/kg n = 4 | DOSE 1.5 mg/kg n = 3 | DOSE .75 mg/kg n = 11 | DOSE .50 mg/kg n = 4 | DOSE .25 mg/kg n = 3 |
|---|---|---|---|---|---|---|
| Liver | 1.53 ± 0.54 | 0.83 ± 0.30 | 0.42 ± 0.06 | 0.70 ± 0.21 | 0.42 ± 0.17 | 0.51 ± 0.24 |
| Spleen | 1.56 ± 0.68 | 0.72 ± 0.25 | 1.25 ± 0.35 | 1.43 ± 0.75 | 1.30 ± 0.59 | 0.85 ± 0.15 |
| Kidney | 0.71 ± 0.19 | 0.66 ± 0.29 | 0.47 ± 0.70 | 0.58 ± 0.11 | 0.54 ± 0.07 | 0.39 ± 0.12 |
| Stomach | 0.62 ± 0.24 | 0.26 ± 0.01 | 0.92 ± 0.12 | 1.05 ± 0.35 | 0.54 ± 0.43 | 0.67 ± 0.38 |
| Small Bowel | 0.96 ± 0.33 | 0.57 ± 0.30 | 0.56 ± 0.08 | 1.70 ± 0.79 | 0.96 ± 0.53 | 0.60 ± 0.13 |
| Skin | 0.25 ± 0.04 | 0.22 ± 0.04 | 0.23 ± 0.06 | 0.50 ± 0.24 | 0.43 ± 0.09 | 0.30 ± 0.03 |
| Tumor | 2.45 ± 1.00 | 0.70 ± 0.43 | 0.36 ± 0.01 | 0.69 ± 0.31 | 0.75 ± 0.39 | 0.37 ± 0.08 |
| Metastasis L. Node | 6.00 ± 3.64 | 4.60 ± 0.50 | 5.65 ± 0.49 | 5.10 ± 3.95 | 3.09 ± 2.24 | 0.54 ± 0.12 |
| Non Metas L. Node | | 1.75 ± 1.06 | | 2.15 ± 0.46 | 2.00 ± 1.80 | 0.83 ± 0.00 |

The values represent the mean +/− the standard deviation of the fluorescence intensity ratios ($I_{630\ nm}/I_{540\ nm}$).

Figure 4:
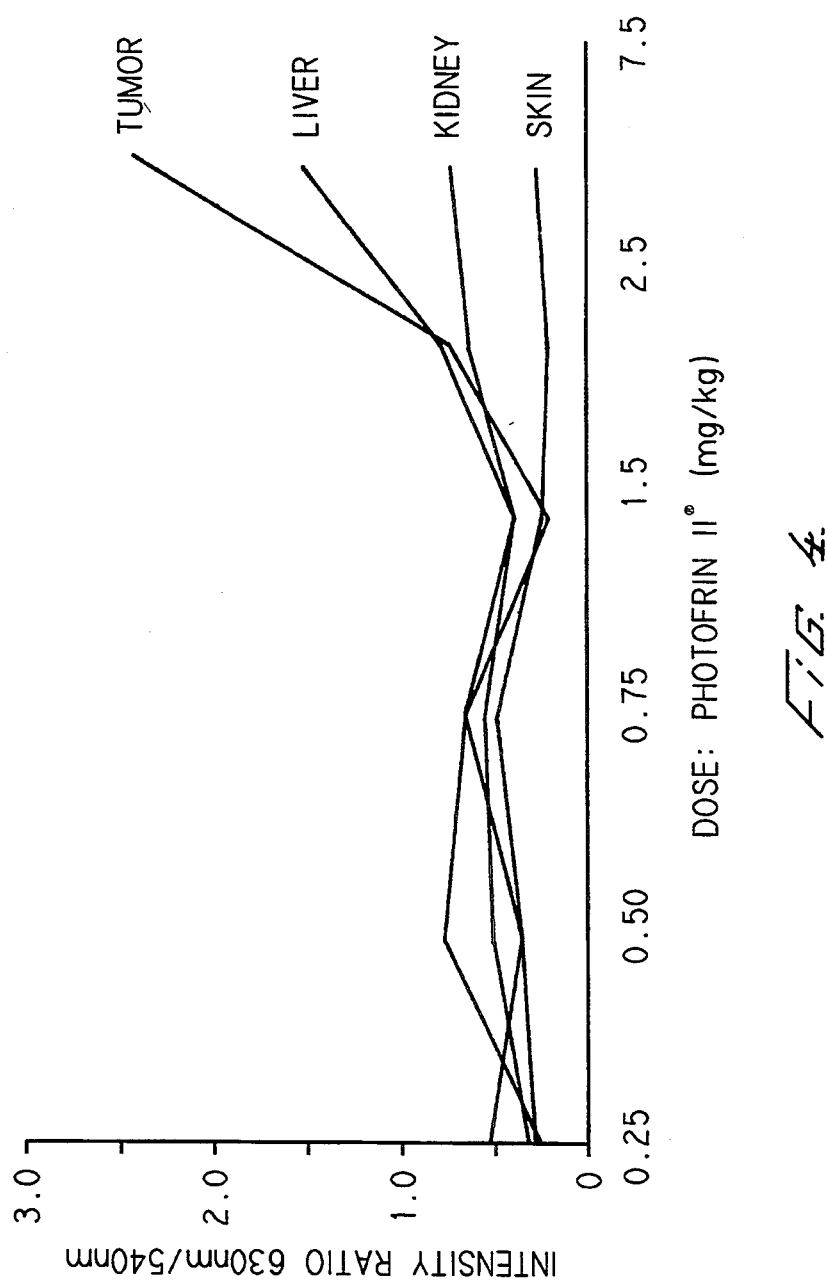
FIG. 4 is a graphic distribution of the fluorescence intensity ratio of Photofrin in specific rat tissues at varying doses.
Figure 5:
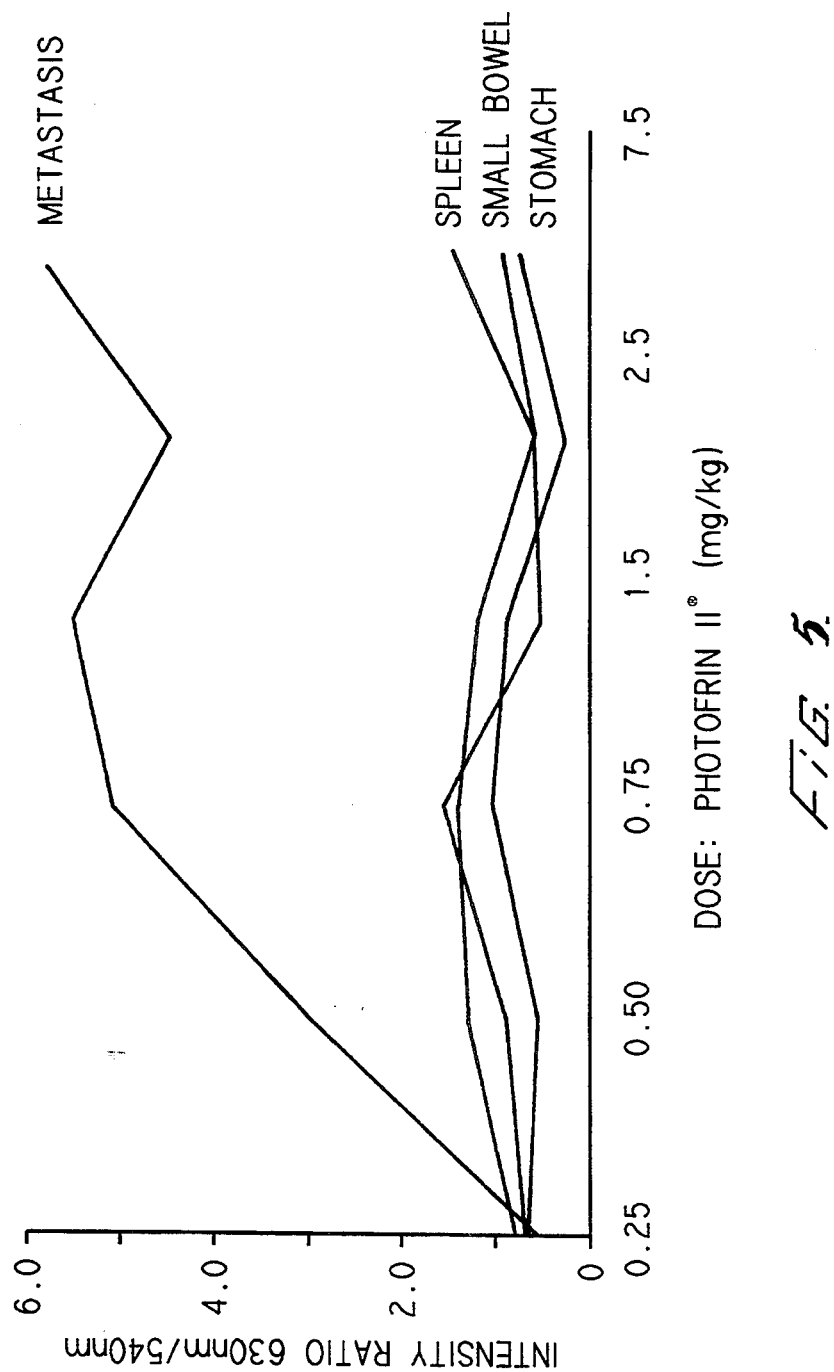
FIG. 5 is a graphic distribution of the fluorescence intensity ratio of Photofrin in specific rat tissues at varying doses.

Table I displays the biodistribution of Photofrin in PA-III adenocarcinoma-bearing rats 48 hours after injecting various doses of the agent. The values represent the fluorescence intensity ratio ($I_{630\ nm}/I_{540\ nm}$), which in turn, is a relative measure of the drug retained in the tissues. The data demonstrates that laser induced fluorescence spectroscopy can distinguish between metastatic and non-metastatic lymph nodes. This selectivity was demonstrated at doses higher than 0.25 mg/kg. The change in the Photofrin fluorescence ratio for various body organs is illustrated in FIGS. 4 and 5, where the smallest intensity ratios are observed in the foot-pad skin.

TABLE II

FLUORESCENCE INTENSITY RATIOS 24 AND 48 HOURS FOLLOWING INJECTION OF 0.75 MG/KG PHOTOFRIN

| TISSUE | 24 HOURS POST INJECTION n = 6 | 48 HOURS POST INJECTION n = 11 |
|---|---|---|
| LIVER | 1.54 ± 0.30 | 0.91 ± 0.47 |
| SPLEEN | 2.00 ± 0.60 | 1.50 ± 0.68 |
| STOMACH | 2.60 ± 0.50 | 1.12 ± 0.54 |
| KIDNEY | 1.39 ± 0.40 | 1.10 ± 0.75 |
| SMALL BOWEL | 2.09 ± 0.28 | 1.90 ± 0.92 |
| SKIN | 0.81 ± 0.15 | 0.51 ± 0.23 |
| METASTASIS | 1.83 ± 1.30 | 8.41 ± 5.44 |

Each value represents mean ± SD as determined in n-number of animals.

Table II illustrates the fluorescence ratios of various organs 24 and 48 hours after injection of 0.75 mg/kg Photofrin. The liver, spleen, kidney, stomach, small bowel and lymph nodes with metastatic neoplasm exhibited a high intensity fluorescence signal, which decreased in time in all tissues except the lymph nodes. However, the intensity ratio of Photofrin in all organs, 48 hours after injection, was higher in PA-III tumor bearing animals than in normal animals. This is illustrated in Table III below.

TABLE III

BIODISTRIBUTION IN *CONTROL (GROUP I) AND PA-III (GROUP II) ANIMALS 48 HOURS AFTER INJECTION OF A 0.75 MG/KG DOSE OF PHOTOFRIN

| TISSUE | GROUP I n = 5 | GROUP II n = 11 |
|---|---|---|
| LIVER | 0.17 ± 0.12 | 0.70 ± 0.21 |
| SPLEEN | 0.50 ± 0.32 | 1.43 ± 0.75 |
| KIDNEY | 0.39 ± 0.18 | 0.58 ± 0.11 |
| STOMACH | 0.45 ± 0.18 | 1.05 ± 0.35 |
| SMALL BOWEL | 0.50 ± 0.40 | 1.70 ± 0.79 |
| SKIN | 0.43 ± 0.19 | 0.50 ± 0.24 |

The values represent mean +/− the standard deviation of the fluorescence intensity ratios ($I_{630\ nm}/I_{540\ nm}$) in n-number of animals.
*Control animals refers to animals that have not been inoculated with PA-III.

B. BPD-MA and Laser Induced Fluorescence Spectroscopy (LIFS)

Two separate experiments were performed to assess the biodistribution of BPD-MA. The first study involved 21 animals and two doses of BPD-MA, 0.25 mg/kg and 0.50 mg/kg, to determine the concentration effect of BPD-MA in various tissues. The second study involved 81 animals and 0.75 mg/kg of BPD-MA to determine the biodistribution of BPD-MA and the sensitivity and specificity of LIFS biodistribution measurements.

intensity ratio increased with increased dose in malignant tissue only.

TABLE IV

BPD-MA BIODISTRIBUTION: DOSE AND TIME DEPENDENCE IN MALIGNANT VS. NON-MALIGNANT TISSUE

| DOSE mg/kg | POST INJECTION TIME | | | |
|---|---|---|---|---|
| | 4 HOURS | | 6 HOURS | |
| | NON-METASTATIC | METASTATIC | NON-METASTATIC | METASTATIC |
| 0.25 | 3.55 ± 1.77 | 3.19 ± 2.31 | 2.77 ± 2.25 | 3.7 ± 2.82 |
| 0.50 | 2.65 ± 0.62 | 6.73 ± 2.39 | | |

The values represent the mean +/− the standard deviation of the fluorescence intensity ratios ($I_{630\ nm}/I_{540\ nm}$) in n-number of animals.

Study #1

BPD-MA (QLT Phototherapeutics, Inc., Vancouver, Canada) was administered to 21 animals intravenously. The animals were divided into three groups of seven animals each and injected with two different doses of BPD-MA, 0.25 mg/kg (n=7) and 0.50 mg/kg (n=7) 4–6 hours prior to surgical exploration. Seven animals served as a control.

The animals were anesthetized with Ketamine 40 mg/kg and Xylazine 5.0 mg/kg intraperitoneally, and the abdomens opened through a midline incision. LIFS exploration of the abdominal and inguinal area was performed. Ipsilateral and contralateral detection was directed to the site of lymph nodes adjacent to the inguinal ligament. From this point, areas were scanned in contact mode along the aorta to the para-aortic and renal lymph nodes (one spectra/16 millaseconds, 3–4 detection sites, going back and forth. Otherwise, the number of sites could increase.) The contralateral site was scanned in the same manner. Metastatic detection was performed during abdominal exploration of the renal, para-aortic, and iliac lymph nodes.

Corrected background fluorescence spectra were obtained in free running mode from the surface of the primary tumor, metastases, as well as from the following organs: liver (L), spleen (Sp), kidney (K), stomach (St), small bowel (SB) and foot-pad skin (S). Suspected malignant tissues were removed for histological examination. The samples were fixed in formalin (10%) and embedded in paraffin.

RESULTS

Figure 6:
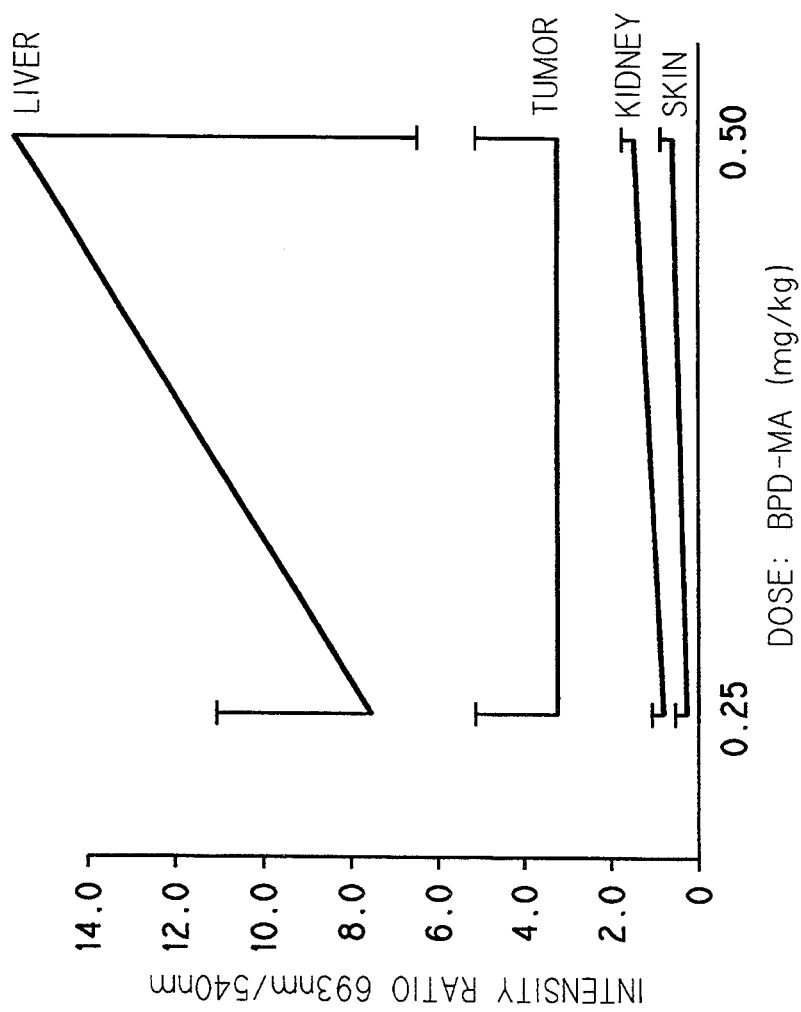
FIG. 6 is a graphic distribution of the fluorescence intensity ratio of BPD-MA in specific rat tissues at 0.25 mg/kg and 0.50 mg/kg doses.
Figure 7:
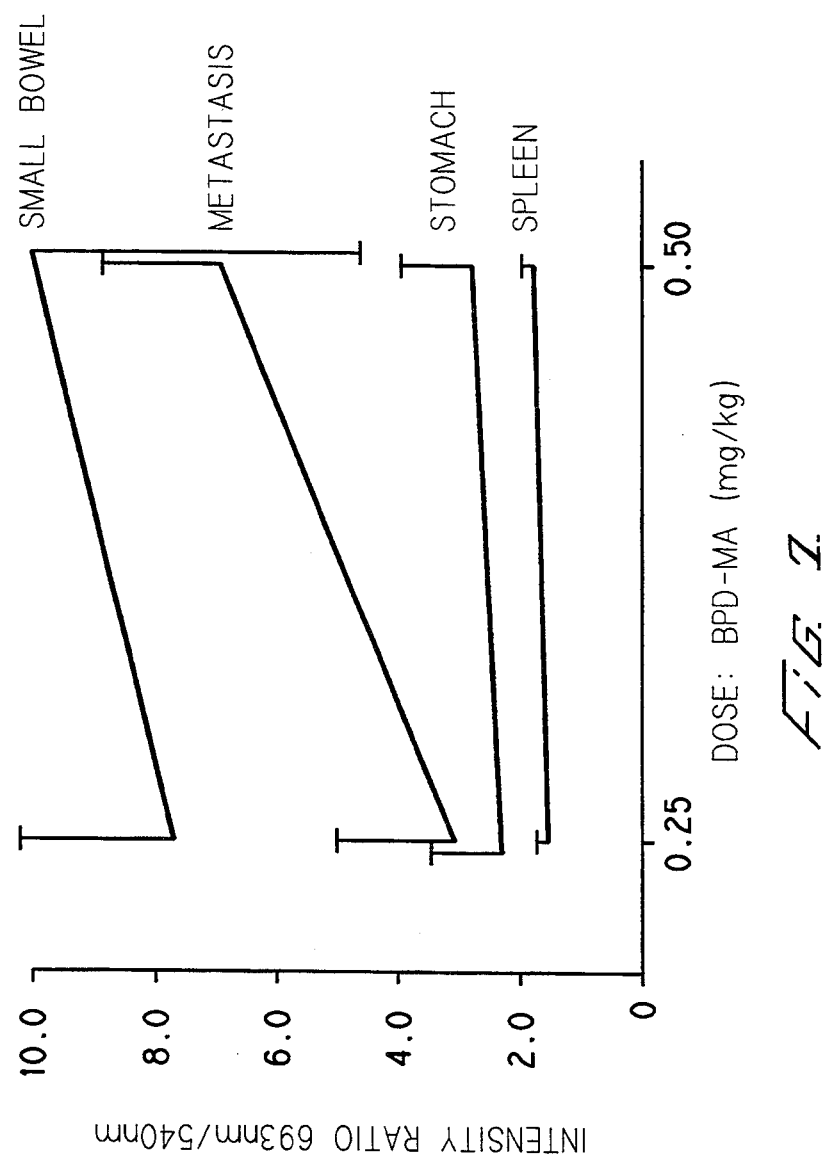
FIG. 7 is a graphic distribution of the fluorescence intensity ratio of BPD-MA specific rat tissues at 0.25 mg/kg and 0.50 mg/kg doses.

Table IV illustrates BPD-MA biodistribution in malignant and non-malignant tissues. Of note, the tissue Table V below demonstrates that BPD-MA biodistribution is influenced by both dose and time. Four hours after injection of either a 0.25 mg/kg dose or a 0.50 mg/kg dose of BPD-MA, the fluorescence intensity ratio was higher in the liver, small bowel, tumor and metastatic tissue as compared to other tissues. Liver and small bowel also had a higher fluorescence intensity ratio than primary tumor and metastasis. In the spleen, kidney, large bowel, muscle and mesenteric lymph nodes (MCLN) the intensity ratio was in the same range. As the dose increased, the tissue intensity ratio also increased. In all instances, however, foot-pad skin exhibited the lowest fluorescence intensity ratio. (FIGS. 6 and 7).

TABLE V

BPD-MA BIODISTRIBUTION: 4 AND 6 HOURS AFTER I.V. INJECTION

| ORGANS | I(690 nm)/I(540 nm) 4 Hours 0.25 mg/kg | I(690 nm)/I(540 nm) 4 Hours 0.50 mg/kg | I(690 nm)/I(540 nm) 6 Hours 0.25 mg/kg |
|---|---|---|---|
| LIVER | 7.83 ± 3.69 | 15.74 ± 9.25 | 5.20 ± 2.38 |
| SPLEEN | 1.29 ± 0.38 | 1.57 ± 0.31 | 1.02 ± 0.16 |
| KIDNEY | 1.04 ± 0.40 | 1.57 ± 0.32 | 0.78 ± 0.19 |
| STOMACH | 2.34 ± 1.20 | 2.95 ± 1.10 | 2.23 ± 0.63 |
| SMALL BOWEL | 7.63 ± 2.73 | 9.91 ± 5.08 | 4.98 ± 2.83 |
| LARGE BOWEL | 1.27 ± 0.30 | 1.59 ± 0.45 | 2.37 ± 1.48 |
| MUSCLE | 1.73 ± 0.47 | 1.62 ± 0.82 | 0.78 ± 0.26 |
| SKIN | 0.31 ± 0.12 | 0.50 ± 0.17 | 0.30 ± 0.15 |
| MCLN | 1.40 ± 0.27 | 3.12 ± 0.99 | 1.43 ± 0.67 |
| TUMOR | 3.37 ± 1.69 | 3.44 ± 1.14 | 1.95 ± 0.37 |
| METAST. L. NODE | 3.19 ± 2.31 | 6.73 ± 2.39 | 3.70 ± 2.82 |
| NON-MET L. NODE | 3.55 ± 1.77 | 2.65 ± 0.62 | 2.77 ± 2.25 |

The values represent the mean +/− the standard deviation of the fluorescence intensity ratios ($I_{690\ nm}/I_{540\ nm}$) in n-number of animals.

Study #2

BPD-MA (QLT Phototherapeutics, Inc., Vancouver, Canada) was administered intravenously in a dose of 0.75 mg/kg to 81 animals 4 hours prior to surgical exploration.

As in Study #1, the animals were anesthetized with Ketamine 40 mg/kg and Xylazine 5.0 mg/kg intraperitoneally, and the abdomens opened through a midline incision. LIFS exploration of the abdominal and inguinal area was performed in contact mode. Metastatic detection was performed during abdominal exploration of the ipsilateral, contralateral and mesenteric lymph nodes. Table VI lists the location of the lymph nodes examined in the study.

TABLE VI

| LOCATION OF THE LYMPH NODES | | |
|---|---|---|
| Left Iliac Lymnph Node | LN | (LILN) |
| Mesenteric I | LN | (MC I) |
| Mesenteric II | LN | (MC II) |
| Right Iliac | LN | (RILN) |

TABLE VI-continued

LOCATION OF THE LYMPH NODES

| | | |
|---|---|---|
| Right Inguinal | LN | (RIN) |
| Right Para-Aortic | LN | (RPAR) |
| Right Sub-Renalis | LN | (RSBR) |
| Right Supra-Renalis | LN | (RSPR) |

The lymph nodes were evaluated in four different ways. A visual examination of the lymph node was made to differentiate normal vs. abnormal lymph nodes. A 3-D size determination of the lymph nodes was also performed in vivo using a digital caliper (Ultra-Call Mark III., Fred V. Fowler Co., Inc., Newton, Mass.) and compared with the visual results. The fluorescence intensity ratio was determined and compared with the visual exam; and the visual exam, the 3-D size determination and the fluorescence intensity ratio were compared. The intraoperative lymph node evaluation is set out schematically below.

| VISUAL | VISUAL & VOLUME | VISUAL & RATIO | VISUAL, VOLUME & RATIO |
|---|---|---|---|

Corrected background fluorescence spectra were obtained in free running mode from the surface of the primary tumor, metastases, as well as from the following organs: liver (L), spleen (Sp), kidney (K), stomach (St), small bowel (SB), large bowel (LB), muscle (M) and foot-pad skin (S).

Sensitivity and specificity of the LIFS biodistribution measurements were computed using a Logistic Regression Analysis. Briefly, sensitivity was defined as the percentage of animals with disease that tested positive, or $A/(A+C)$. Specificity was defined as the percentage of animals without disease that tested negative, or $D/(B+D)$. Inflammatory and normal tissues were scored as $\ominus$, non-metastatic. Metastatic tissues were scored as $\oplus$.

| | DISEASE | |
|---|---|---|
| | + | − |
| TEST + | A | B |
| TEST − | C | D |

B represents a false positive.
C represents a false negative.

RESULTS

TABLE VII

SENSITIVITY/SPECIFICITY FOR METASTATIC VS. NON-METASTATIC (NORMAL + INFLAMMATORY) LYMPH NODES FOR VARIOUS MODELS USING LOGISTIC REGRESSION INTRAOPERATIVE EVALUATION OF LYMPH NODES

| SENSITIVITY | SENSITIVITY/SPECIFICITY | | |
|---|---|---|---|
| VISUAL | VISUAL + VOLUME | VISUAL + RATIO | VISUAL + VOLUME + RATIO |
| 70% | 68.5/99.9 | 72.5/97.2 | 70.0/99.9 |
| 77% 96.6 | 77.5/99.5 | 77.0/96.6 | 77.0/99.8 |
| 80% | 80.5/90.7 | 80.5/94.1 | 80.0/99.0 |
| 90% | 89.0/85.5 | 91.0/75.5 | 91.0/88.0 |
| 95% | 97.0/41.7 | 95.0/51.6 | 94.5/77.0 |

Of note, Table VII illustrates that the error of detection was only 1% for the 80% of diseased animals that tested positive.

TABLE VIII

INTENSITY RATIO ANALYSIS OF BPD-MA IN LYMPH NODES
RATIO SUMMARY FOR LYMPH NODES BY HISTOLOGY

| HISTOLOGY | NUMBER OF OBSERVATION | RATIO MEAN | RATIO SD |
|---|---|---|---|
| INFLAMMATORY LN | 614 | 3.67 | 4.02 |
| METASTATIC LN | 206 | 6.26 | 4.91 |
| NORMAL LN | 200 | 3.06 | 2.30 |

Figure 8:
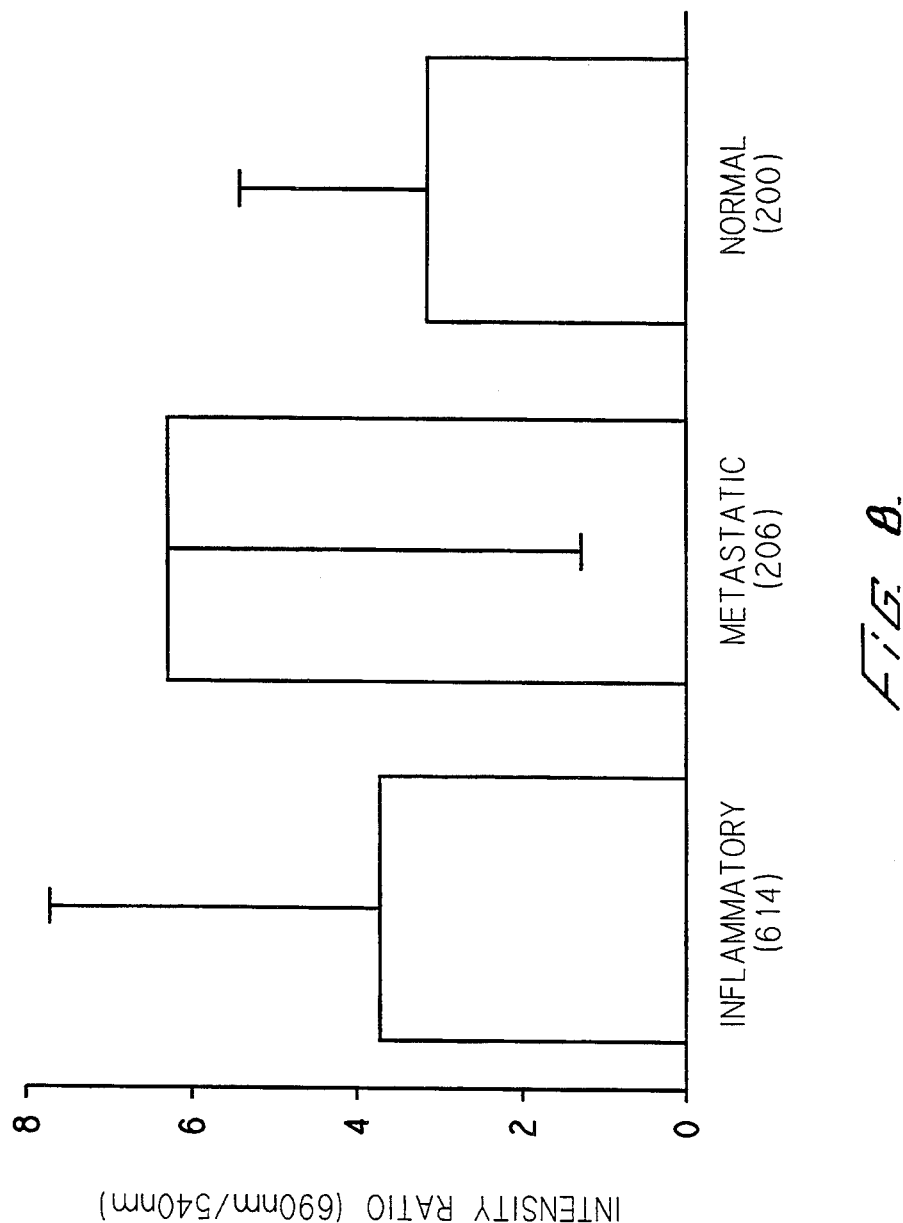
FIG. 8 is a graphic distribution summarizing the fluorescence intensity ratio of BPD-MA in rat lymph nodes categorized by histology.

Table VIII above summarizes the fluorescence intensity ratio for lymph nodes categorized by histology. As illustrated, the metastatic lymph nodes displayed a greater fluorescence intensity ratio than normal or inflamed lymph nodes. (See FIG. 8).

TABLE IX

INTENSITY RATIO ANALYSIS OF BPD-MA IN LYMPH NODES
RATIO SUMMARY FOR LYMPH NODES BY LOCATION

| LOCATIONS | NUMBER OF OBSERVATION | RATIO MEAN | RATIO SD |
|---|---|---|---|
| Left Iliac LN (LILN) | 230 | 5.22 | 4.76 |
| Mesenteric I LN (MC I) | 229 | 2.45 | 1.80 |
| Mesenteric II LN (MC II) | 220 | 2.37 | 1.79 |
| Right Iliac LN (RILN) | 233 | 5.86 | 5.33 |
| Right Inguinal LN (RIN) | 18 | 4.72 | 2.41 |
| Right Para-Aortic LN (RPAR) | 24 | 7.40 | 6.00 |
| Right Sub-Renalis LN (RSBR) | 45 | 4.50 | 2.94 |
| Right Supra-Renalis LN (RSPR) | 11 | 4.26 | 3.19 |

Figure 9:
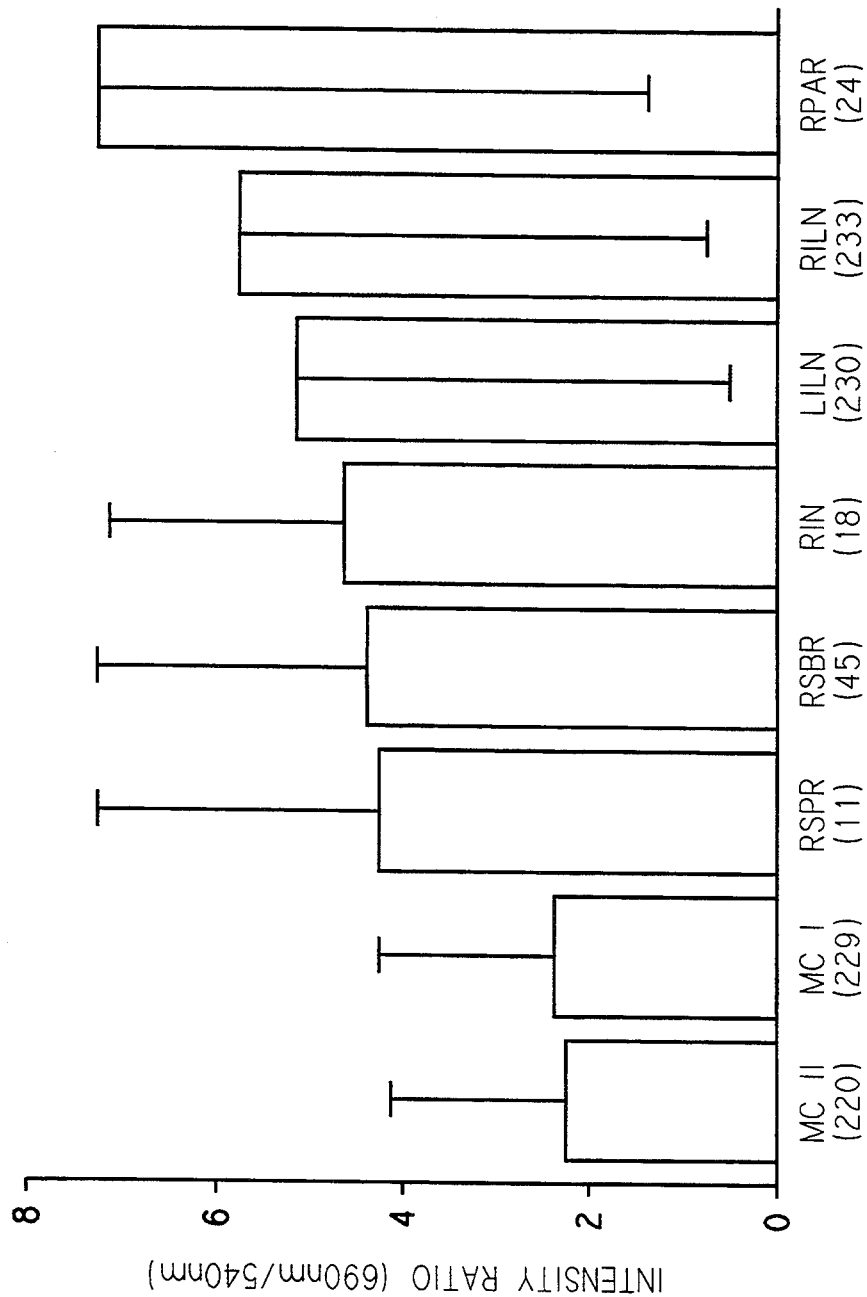
FIG. 9 is a graphic distribution summarizing the fluorescence ratio of BPD-MA in rat lymph nodes categorized by location.

Table IX summarizes the fluorescence intensity ratio for lymph nodes categorized by location. Regardless of location, metastatic lymph nodes exhibited a greater fluorescence intensity ratio than normal lymph nodes. (See FIG. 9).

TABLE X

INTENSITY RATIO ANALYSIS OF BPD-MA
RATIO SUMMARY FOR ORGANS, PRIMARY TUMOR AND LYMPH NODES

| SITE | NUMBER OF OBSERVATION* | RATIO MEAN | RATIO SD |
|---|---|---|---|
| Skin (SK) | 214 | 0.09 | 0.03 |
| Kidney (KY) | 226 | 1.16 | 0.43 |
| Muscle (MS) | 228 | 1.84 | 1.05 |
| Large Bowel (LB) | 231 | 1.87 | 0.75 |
| Spleen (SP) | 229 | 2.25 | 1.27 |
| Lymph Nodes (LN) | 995 | 3.79 | 3.05 |
| Primary Tumor (PT) | 215 | 4.14 | 2.19 |
| Stomach (ST) | 227 | 4.28 | 1.89 |
| Small Bowel (SB) | 224 | 4.44 | 3.78 |
| Liver (LV) | 227 | 13.60 | 6.17 |

*Number of observations included replicates for each rat.

Figure 10:
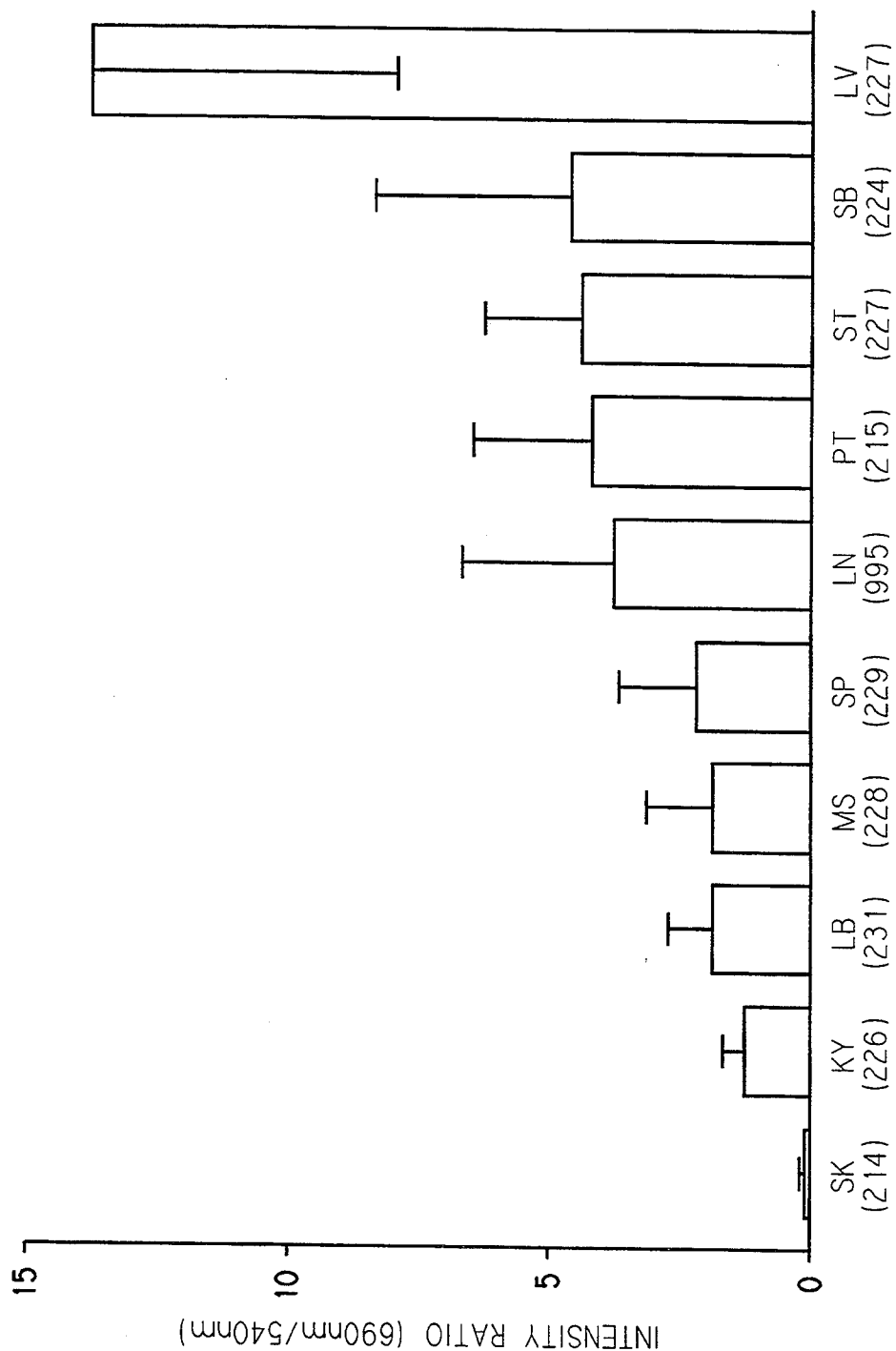
FIG. 10 is a graphic distribution summarizing and comparing the fluorescence intensity ratio of BPD-MA in specific rat organs, primary tumor and lymph nodes.

The fluorescence intensity ratio for organs, primary tumor and lymph nodes is summarized and compared in tabular form in Table X above, and graphically in FIG. 10. As illustrated, skin exhibited the lowest fluorescence intensity ratio. Tumor and lymph nodes exhibited a higher ratio that skin, kidney, muscle, large bowel and spleen, and the ratios for liver, small bowel and stomach were higher than all other tissues.

DISCUSSION

The biodistribution of Photofrin and BPD-MA was determined by LIFS in an animal tumor model with unilateral metastatic spread. Photofrin was administered by the intraperitoneal route 24 and 48 hours prior to detection in doses varying from 0.25 to 7.5 mg/kg. A Helium-cadmium laser (442 nm) was used as an excitation source via a 400 micron core diameter fiber. Through the same fiber, reflected and emitted light was guided to a spectrograph. Spectra of liver, spleen, kidney, stomach, small bowel, large bowel, muscle, foot-pad skin, primary tumor, metastatic lymph nodes and non-metastatic lymph nodes were acquired and analyzed by an optical multi-channel analyzer. The intensity ratio (R) of the characteristic fluorescence peak of Photofrin (~630 nm) to the autofluorescence intensity was used as an index for drug presence. It was found that R-metastasis>R-primary tumor>R-skin. Also, R-(L, S, K, St and SB) was high compared with R-tumor. Hence, the high fluorescence intensity ratios obtained from primary tumor, liver, spleen, kidney, stomach and small bowel indicate high drug accumulation in these organs. Skin tissue displayed the lowest fluorescence intensity ratios, indicative of the small amount of drug retained by skin tissue; whereas metastatic lymph nodes displayed the highest fluorescence intensity ratios, indicative of the large amount of drug retained by metastatic lymph nodes.

BPD-MA was administered intravenously in doses of 0.25 and 0.50 and 0.75 mg/kg 4–6 hours before detection. Using the same set-up described above for Photofrin, spectra were obtained from tumor, skin, muscle, liver, kidney, spleen, stomach, small bowel and large bowel. The corresponding intensity ratio (R=($I_{690\,nm}$/$I_{540\,nm}$) was used as an index to measure the fluorescence intensity of BPD-MA. The data reveal that BPD-MA concentration was higher in tumors and lymph nodes than in skin, kidney, muscle, large bowel and spleen. The fluorescence intensity ratio of metastatic lymph nodes was higher than that of normal lymph nodes, and higher than all other tissues except the liver. Skin exhibited the lowest fluorescence intensity ratio, indicative of the small drug concentration in this tissue. On the other hand, liver, small bowel and stomach intensity ratios were higher than all other tissues. This may be due to the BPD-MA elimination pathway through the liver, bile and small bowel. BPD-MA retention in all organs decreased with time.

These results are consistent with results obtained using radiolabelled photosensitizers for biodistribution analysis, yet, without the hazards and disadvantages that accompany the use of radiolabels. Hence, LIFS is an alternative method for determining the biodistribution of drugs in tissue. Moreover, LIFS is less hazardous, less time-consuming and provides immediate results than current procedures for performing biodistribution analysis.

We claim:

1. A method for determining the biodistribution of a substance in a body comprising:
   a) administering an effective amount of a substance capable of light-induced fluorescence to tissue to be examined and to tissue whose condition is known;
   b) exciting said tissue to be examined and said tissue whose condition is known with a beam of light from a light source to cause said substance to emit fluorescence;
   c) measuring said fluorescence emitted from said tissue to be examined and said tissue whose condition is known each at a first wavelength and a second wavelength;
   d) calculating a first fluorescence intensity ratio for said examined tissue and a second intensity ratio for said tissue whose condition is known, wherein said intensity ratios are said fluorescence at said first wavelength divided by said fluorescence at said second wavelength; and
   e) comparing said first intensity ratio with said second intensity ratio and thereby determining the biodistribution of said substance.

2. The method of claim 1 wherein determining the biodistribution of a substance in a body further comprises producing a first signal corresponding to the first fluorescence intensity ratio and a second signal corresponding to the second fluorescence intensity ratio and then displaying said first and second signals.

3. The method of claim 1 wherein said substance is intrinsically fluorescent.

4. The method of claim 1 wherein said substance is labelled with an extrinsic fluorophor by connecting said fluorophor to said substance.

5. The method of claim 1 wherein said light source is a laser.

6. The method of claim 1 wherein said light source is an arc lamp.

7. The method of claim 1 wherein said beam of light is filtered to a specific wavelength.

8. The method of claim 1 wherein said beam of light is at least substantially monochromatic.

9. The method of claim 1 wherein said beam of light is incoherent light.

10. The method of claim 1 wherein said beam of light is at least substantially monochromatic and further comprises incoherent light.

* * * * *